United States Patent [19]

Dales

[11] 4,368,334

[45] Jan. 11, 1983

[54] P-HYDROXYMANDELIC ACID

[75] Inventor: John R. M. Dales, Littlehampton, England

[73] Assignee: Beecham Group Limited, England

[21] Appl. No.: 233,606

[22] PCT Filed: Aug. 8, 1980

[86] PCT No.: PCT/GB80/00126

§ 371 Date: Apr. 9, 1981

§ 102(e) Date: Jan. 23, 1981

[87] PCT Pub. No.: WO81/00404

PCT Pub. Date: Feb. 19, 1981

[30] Foreign Application Priority Data

Aug. 9, 1979 [GB] United Kingdom ............... 7927829

[51] Int. Cl.$^3$ ............................................. C07C 59/50
[52] U.S. Cl. ............................... 562/470; 260/501.1
[58] Field of Search ........................... 562/470, 472; 260/501.1

[56] References Cited

U.S. PATENT DOCUMENTS 3,725,437  4/1973  Nagoya et al. ................. 562/470

FOREIGN PATENT DOCUMENTS

| 3825 | 2/1978 | European Pat. Off. ............. 478/ |
| 32558 | 11/1964 | Fed. Rep. of Germany ...... 562/470 |
| 2040218 | 2/1972 | Fed. Rep. of Germany ...... 562/470 |
| 53-5092344 | 12/1978 | Japan ............................. 562/478 |

*Primary Examiner*—Paul J. Killos
*Attorney, Agent, or Firm*—Jacobs & Jacobs

[57] ABSTRACT

A process for the isolation of a solid salt of p-hydroxymandelic acid, which process comprises reacting phenol with glyoxylic acid in the presence of sodium or potassium hydroxide, acidifying to a pH less than 3, extracting the resulting solution with a water-immiscible solvent to provide a solution of p-hydroxymandelic acid and precipitating the salt therefrom.

10 Claims, No Drawings

P-HYDROXYMANDELIC ACID

This invention relates to a chemical process, and in particular to a process for the isolation of a salt of p-hydroxymandelic acid. It also relates to novel salts which may be isolated by this process.

Salts of p-hydroxymandelic acid are valuable intermediates, for example for the preparation of p-hydroxyphenylglycine, which is useful for the manufacture of the penicillin derivative, amoxycillin.

British Pat. Specification No. 1,377,243 discloses in Example 5(b) thereof the preparation of a solution of the sodium salt of p-hydroxymandelic acid (referred to therein as 4-hydroxyphenylglycolic acid), but this salt is not isolated.

One method for the isolation of the salt is disclosed in Belgium Pat. No. 867,287 which describes a process for the manufacture of solid sodium or potassium p-hydroxymandelate monohydrate which comprises reacting by known means phenol with glyoxylic acid in the presence of, respectively, sodium or potassium hydroxide, followed by adjustment of the pH of the solution to between 5 and 7 and salting out of the desired sodium or potassium salt with respectively, a sodium or potassium salt of a simple acid.

We have now found an advantageous method for the isolation of solid salts of p-hydroxymandelic acid prepared in this way, by precipitation from an organic solution of the acid. This method of isolation produces a higher yield of isolated salt than the method described in Belgium Pat. No. 867,287.

Accordingly the present invention provides a process for the isolation of a solid salt of p-hydroxymandelic acid, which process comprises reacting phenol with glyoxylic acid in the presence of sodium or potassium hydroxide, acidifying to a pH less than 3, extracting the resulting solution with a water-immiscible solvent to provide a solution of p-hydroxymandelic acid and precipitating the salt therefrom.

The reaction between phenol and glyoxylic acid may be carried out in any convenient way. Suitable conditions described in Belgium Pat. No. 867,287 and also in Example 5(b) of British Pat. No. 1,377,243. Suitably the reaction is carried out at a temperature in the range 20°-100° C., suitably 20°-60° preferably 30°-40° C. We have found that it is also preferable to adjust the dilution of the reaction solution so that the concentration of glyoxylic acid is in the range 3 to 9% w/v, preferably 3.5 to 7%, especially 3.5 to 4.5% w/v. The reaction may advantageously be carried out under nitrogen.

The reaction is normally carried out for a time from 3 to 8 hours, suitably about 4 hours.

Suitably the phenol is employed in excess. Preferably the concentration of phenol employed is in the range 13 to 20% w/v. The sodium or potassium hydroxide is employed in a quantity related to the amount of phenol used and is conveniently employed at a concentration of from 5 to 8% w/v in the reaction mixture.

When the reaction is complete excess phenol is removed by conventional means with a solvent and the reaction mixture is then acidified, for example with hydrochloric or sulphuric acid, to a pH of less than 3. Preferably the pH is adjusted to 1 to 2. This acidified reaction mixture is then extracted with a water-immiscible solvent. Examples of suitable solvents include methyl ethyl ketone, methyl isobutyl ketone, ethyl acetate, or methyl acetate, or mixtures of such solvents. A preferred solvent is methyl isobutyl ketone.

This solvent extraction may be carried out in any conventional way, preferably by counter-current technique.

This extraction results in p-hydroxymenadelic acid being extracted into the water-immiscible phase. The aqueous phase is discarded. The required salt is precipitated from the water-immiscible solution by adding a suitable precipitating agent, depending on the particular salt. For preparing the sodium salt, suitable precipitating agents include sodium hydroxide in aqueous or alcoholic solution, or sodium ethyl hexanoate in a suitable organic solvent. A solution of potassium ethyl hexanoate would be a suitable precipitating agent for preparing the potassium salt. The ammonium salt may conveniently be precipitated by the addition of ammonia gas. Substituted ammonium salts can be precipitated by adding the corresponding amine itself, or a solution, thereof.

With respect to the ammonium and substituted ammonium salts of p-hydroxymandelic acid, these salts cannot be isolated from a reaction between phenol and glyoxylic acid by the salting out procedure disclosed in Belgium Pat. No. 867,287. The present invention therefore enables these salts to be isolated from this process for the first time.

Accordingly, this invention also provides, as novel compounds solid ammonium and substituted ammonium salts of p-hydroxymandelic acid.

A preferred salt to precipitate in the process of this invention is the ammonium salt, because it is precipitated the most efficiently and the addition of ammonia gas is easy to control.

Substituted ammonium salts which may be prepared by the process of this invention include salts with primary, secondary or tertiary alkyl amines, preferably $C_1$ to $C_6$ alkylamines, for example triethylamine, sec-butylamine, t-butylamine, and cyclohexylamine.

The salts prepared according to the process of this invention may be converted to p-hydroxyphenylglycine by reaction with ammonia or a salt thereof as described in Belgium Pat. No. 869,021. When a substituted ammonium salt of p-hydroxymandelic acid is employed, some N-substituted p-hydroxyphenylglycine will also be produced, and it is preferable to react the substituted ammonium salts with the correspondingly substituted amine to produce an N-substituted p-hydroxyphenylglycine.

For the preparation of p-hydroxyphenylglycine itself, it is preferable to use the sodium, potassium or ammonium salt of p-hydroxymandelic acid.

The following Examples illustrate the present invention.

EXAMPLE 1

Preparation of Ammonium p-Hydroxymandelate

A mixture of phenol (1,098 g) aqueous glyoxylic acid (50% w/w solution, 720 ml) and water (3 l) are stirred at 15° C. To the solution was added sodium hydroxide solution (50% w/w) the temperature being maintained at 15° C.±2° C., until the solution reached pH 10.5. The reaction mixture was then heated to 35° C. for 3 hours.

The solution was adjusted to pH7 by addition of concentrated hydrochloric acid the temperature being maintained at 35° C. during the addition. The mixture was extracted at 35° C. with methyl isobutyl ketone (2×1.2 l) to remove excess phenol.

The aqueous phase was adjusted to pH2 with concentrated hydrochloric acid and the solution temperature reduced to 20° C. The aqueous phase containing p-hydroxymandelic acid was continuously extracted with methyl isobutyl ketone in a counter-current extractor at an organic to aqueous flow rate of 3 to 2.

After extraction, ammonia gas was passed into the stirred organic phase until no more precipitation of ammonium mandelate occurred. The product was filtered off and the ammonium mandelate cake suctioned as dry as possible before drying under vacuum at 40° C.

Product weighed 837.5 g with an activity yield of 58.1%.

EXAMPLE 2

Preparation of Sodium p-Hydroxymandelate

The procedure of Example 1 was repeated except that the organic phase containing p-hydroxymandelic acid was treated with a molar equivalent of sodium hydroxide as a 50% w/w aqueous solution. The caustic solution was added over one hour during which time the methyl isobutyl ketone solution was maintained at about 20° C. with cooling. The precipitate of sodium p-hydroxymandelate monohydrate was filtered off and suctioned as dry as possible before drying under vacuum at 40° C.

Product weighed 772.8 g, activity yield 53.5%.

EXAMPLE 3

Preparation of Ammonium p-Hydroxymandelate

Aqueous glyoxylic acid (50% w/w, 534 g) was added dropwise over 30 minutes to a stirred solution of phenol (1,014 g) and sodium hydroxide (397 g) in water (4.5 l) at 35° C. The mixture was then stirred at 35° C. for 4 hours. The solution was adjusted to pH7 with concentrated hydrochloric acid the temperature being maintained at 35° C. during the addition. The solution was extracted with methyl isobutyl ketone (3×600 ml) at 35° C. to remove excess phenol. The aqueous phase was adjusted to pH2 with concentrated hydrochloric acid and cooled to 20° C. The aqueous phase containing p-hydroxymandelic acid was continuously extracted with methyl isobutyl ketone in a counter-current extraction using an organic to aqueous flow rate of 2 to 1.

After extraction, ammonia gas was passed into the organic phase containing the p-hydroxymandelic acid until no more precipitation of ammonium p-hydroxymandelate occurred. The solid was filtered off and suctioned as dry as possible before drying under vacuum at 40° C.

Product weighed 578.3 g, activity yields 72.7%.

EXAMPLE 4

Preparation of Sodium p-Hydroxymandelate

Sodium hydroxide solution (50% w/w, ca 650 ml) was added dropwise over about one hour to a stirred mixture of phenol (1.098 kg), aqueous glyoxylic acid (50% w/w solution, 720 ml) and water (3 l) at 15° C. until a pH of 10.5 had been reached. The reaction mixture was then stirred and tested at 35° C. for 3 hours. The solution was adjusted to pH7 with concentrated hydrochloric acid and extracted at 35° C. with methyl isobutyl ketone to remove excess phenol. The aqueous solution was adjusted to pH2 with concentrated hydrochloric acid and continuously extracted in a counter-current extractor with ethyl acetate at an organic to aqueous flow rate of 1 to 1.

After extraction the organic phase was treated with a molar equivalent of a 50% w/w solution of sodium hydroxide. The resulting precipitate of sodium p-hydroxymandelate monohydrate was stirred for 30 minutes at 20° C. and then filtered off under vacuum. The product was dried under vacuum at 40° C.

Product weighed 714.2 g, activity yield 50%.

EXAMPLE 5

Preparation of the t-Butylamine Salt of p-Hydroxymandelic Acid

Sodium hydroxide solution (50% w/w, 140 ml) was added dropwise over 20 minutes to a stirred solution of phenol (183 g), aqueous glyoxylic acid (50% w/w solution, 137 ml) and water (500 ml) at between 10° C. to 15° C. The resulting mixture was then stirred at 35° C. for 7 hours. The solution was adjusted to pH7 with concentrated hydrochloric acid and extracted at 35° C. with methylene dichloride (1×200 ml and 2×75 ml). The solution was adjusted to pH2 with concentrated hydrochloric acid and extracted continuously in a liquid/liquid extractor with ethyl acetate (2.25 l) for 2 hours.

The resulting ethyl acetate phase was stirred and treated with an excess of t-butylamine (108 ml). The precipitate was stirred for 30 minutes and then filtered off. The cake was washed with ethyl acetate (200 ml) and the product, dried under vacuum at 40° C.

Weight yield of t-butylamine salt was 166.5 g.

EXAMPLE 6

Preparation of the t-Butylamine salt of p-Hydroxymandelic Acid

The procedure of Example 5 was repeated except that methyl isobutyl ketone was used as the extraction solvent.

The resulting methyl isobutyl ketone solution was stirred and treated with an excess of t-butylamine (85 ml). The precipitate was stirred for 30 minutes and then filtered off. The cake was washed with MIBK (200 ml) and the product was dried under vacuum at 40° C. The weight yield of t-butylamine salt was 152 g.

EXAMPLE 7

Preparation of the Cyclohexylamine Salt of p-Hydroxymandelic Acid

By the procedure of Example 6 the cyclohexylamine salt was prepared by treating the methyl isobutyl ketone solution with an excess of cyclohexylamine (92 ml). The weight yield of cyclohexylamine salt was 168 g.

EXAMPLE 8

Preparation of the sec-Butylamine salt of p-Hydroxymandelic Acid

By the procedure of Example 6 the sec-butylamine salt was prepared by treating the methyl isobutyl ketone solution with an excess of sec-butylamine (80 ml). The weight yield of sec-butylamine salt was 149.5 g.

EXAMPLE 9

Preparation of the triethylamine salt of p-Hydroxymandelic Acid

By the procedure of Example 6 the triethylamine salt was prepared by treating the methyl isobutyl ketone solution with an excess of triethylamine (112 ml). The solution was stirred for 30 minutes with cooling and then left to stand at 3° C. for 16 hours. The precipitate was filtered off and the cake washed with cold methyl isobutyl ketone (200 ml). The product was dried under vacuum at 40° C. The weight yield of triethylamine salt was 138.6 g.

EXAMPLE 10

Preparation of potassium p-Hydroxymandelate

By the procedure of Example 6 the potassium salt was prepared by treating the methyl isobutyl ketone solution with an excess of a 2 N solution of potassium ethyl hexanoate in methyl isobutyl ketone (400 ml). The weight yield of potassium p-hydroxymandelate was 129 g.

I claim:

1. A process for the isolation of a solid salt of p-hydroxymandelic acid, which process comprises reacting phenol with glyoxylic acid in the presence of sodium or potassium hydroxide, acidifying to a pH less than 3, extracting the resulting solution with a water-immiscible solvent to provide a solution of p-hydroxymandelic acid and precipitating the salt therefrom.

2. A process as claimed in claim 1 wherein the concentration of glyoxylic acid in the reaction solution is in the range of 3.5 to 7% weight-volume.

3. A process as claimed in claim 1, wherein the concentration of glyoxylic acid in the reaction solution is in the range 3.5 to 4.5% weight/volume.

4. A process as claimed in claim 1, wherein the acidified reaction solution is extracted with methyl ethyl ketone, methyl isobutyl ketone, ethyl acetate, methyl acetate or mixtures thereof.

5. A process as claimed in claim 4 wherein the acidified reaction solution is extracted with methyl isobutyl ketone.

6. A process as claimed in claim 1, wherein the solid salt of p-hydroxymandelic acid is the ammonium salt.

7. A process as claimed in claim 6 wherein ammonium p-hydroxymandelate is precipitated by the addition of ammonia gas.

8. A process as claimed in claim 1, wherein the solid salt of p-hydroxymandelic and is a substituted ammonium salt.

9. A process as claimed in claim 8 wherein the substituted ammonium salt of p-hydroxymandelic acid is precipitated by the addition of the corresponding amine or a solution thereof.

10. The solid ammonium or substituted ammonium salt of p-hydroxymandelic acid.

* * * * *